United States Patent [19]

Zahler

[11] Patent Number: 4,548,747
[45] Date of Patent: Oct. 22, 1985

[54] 3-ACYLAMINO-1-SULFONYLAMINOCARBONYLMETHOXY-2-AZETIDINONES

[75] Inventor: Robert Zahler, Princeton, N.J.

[73] Assignee: E. R. Squibb & Sons, Inc., Princeton, N.J.

[21] Appl. No.: 490,274

[22] Filed: May 2, 1983

[51] Int. Cl.[4] .................. C07D 205/08; C07D 401/12; C07D 403/12; A61K 31/395

[52] U.S. Cl. .......................... 260/239 A; 260/239.3 R; 260/245.4; 260/330.3; 260/330.9; 544/182; 544/215; 544/279; 544/327; 544/335; 544/336; 544/359; 546/208; 546/275; 514/210

[58] Field of Search....... 260/329 AL, 245.4, 239.3 R 330.3, 330.9; 544/182, 215, 279, 327, 335, 336, 359; 546/208, 275

[56] References Cited

U.S. PATENT DOCUMENTS 4,337,197  6/1982  Gordon et al. ................. 260/239 A

FOREIGN PATENT DOCUMENTS 2071650  9/1981  United Kingdom .

*Primary Examiner*—Mark L. Berch
*Attorney, Agent, or Firm*—Lawrence S. Levinson; Donald J. Barrack

[57] ABSTRACT

Antibacterial activity is exhibited by βlactams having a 3-acylamino substituent and in the 1-position a group of the formula

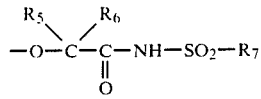

wherein $R_5$ and $R_6$ are the same or different and each is hydrogen, alkyl, alkenyl, alkynyl, phenyl, substituted phenyl, cycloalkyl or $R_c$, or $R_5$ and $R_6$ together with the carbon atom to which they are attached are cycloalkyl or $R_c$, or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxyl, —$CH_2X_1$, —$S$—$X_2$, —$O$—$X_2$, or

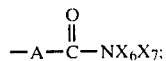

and $R_7$ is alkyl, substituted alkyl, phenyl or substituted phenyl; and $R_c$ is 4,5,6 or 7-membered heterocycle.

12 Claims, No Drawings

3-ACYLAMINO-1-SULFONYLAMINOCARBONYL-METHOXY-2-AZETIDINONES

RELATED APPLICATIONS

U.S. patent application Ser. No. 404,945, filed Aug. 4, 1982, now abandoned discloses that β-lactams having a

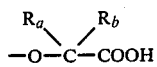

substituent (or an ester or pharmaceutically acceptable salt thereof) in the 1-position and an acylamino substituent in the 3-position exhibit activity against a range of gram-negative and gram-positive bacteria.

U.S. patent application Ser. No. 364,562, filed Apr. 1, 1982, discloses that β-lactams having a

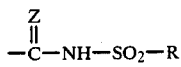

substituent in the 1-position and an acylamino substituent in the 3-position exhibit activity against a range of gram-negative and gram-positive bacteria.

BACKGROUND OF THE INVENTION

The β-lactam ring,

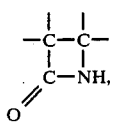

has been known since the late nineteenth century. While knowledge of β-lactam chemistry developed during the early 1900's, it was not until 1929 that Fleming reported in *Brit. J. Exper. Pathol.*, 10, 226 (1929) that a fermentation product of the organism *Penicillium notatum* had antibiotic properties. The compound which Fleming had worked with was benzylpenicillin,

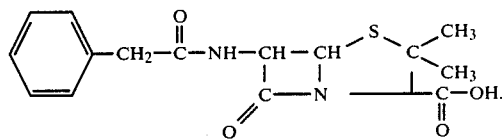

The in vivo activity of benzylpenicillin against various bacteria was reported by Chain et al. in *Lancet*, 2:226 (1940).

During the early 1940's research in the field of penicillins was intense. This research focused first on structure elucidation and then on synthetic routes for preparing benzyl penicillin. It was not, however, until the late 1950's that a totally synthetic route was discovered for the preparation of benzyl penicillin.

U.S. Pat. No. 2,941,955, issued June 21, 1960, to Doyle et al., discloses the discovery of 6-aminopenicillanic acid,

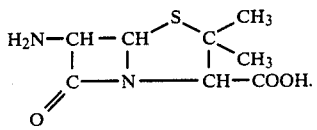

This patent was followed by U.S. Pat. No. 2,951,839, issued Sept. 6, 1960, also to Doyle et al., which discloses the use of 6-aminopenicillanic acid as a valuable intermediate which could be acylated, using art-recognized procedures, to obtain penicillin derivatives having antibiotic properties. Using 6-aminopenicillanic as a stepping stone, research chemists have prepared numerous penicillin derivatives having antibiotic activity.

The second major class of β-lactam antibiotics is the cephalosporins. In the 1940's a Cephalosporium species was found to produce an antibiotic that had activity against gram-positive and gram-negative bacteria. Work in the 1950's showed that the fermentation product of a Cephalosporium species contained not one, but several antibiotics. One of these antibiotics, cephalosporin C,

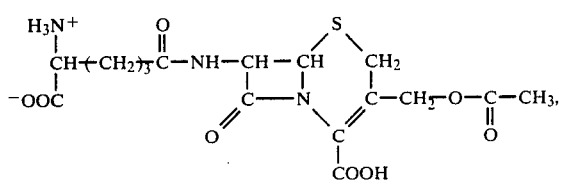

proved to be an important stepping stone in cephalosporin research. Removal of the acyl group in the 7-position of cephalosporin C yields 7-aminocephalosporanic acid.

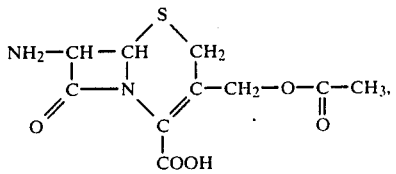

an intermediate useful for the preparation of numerous acylated compounds which are analogs of cephalosporin C.

The penicillins and cephalosporins are, of course, the most important of the β-lactam antibiotics reported to date. Others have, however, been reported. Stapley et al., *Antimicrobial Agents and Chemotherapy*, 2(3):122 (1972) disclose that certain actinomycete cultures isolated from soil produce antibiotics characterized by a methoxy group and a D-α-aminoadipic acid on the 7-carbon of the cephem nucleus. The cephamycins, as they are known, have the formula

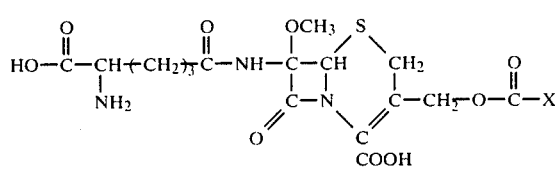

cephamycin A: X=

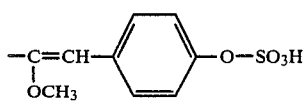

cephamycin B: X=

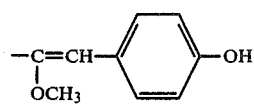

cephamycin C: X=—NH₂

Stapley et al. reported that cephamycin A and cephamycin B each exhibits a similar range of potencies against gram-negative and gram-positive bacteria, and cephamycin C had greater potency against gram-negative bacteria than against gram-positive bacteria. Cephamycin C was reported to be the most active of the three antibiotics.

Scannell et al., *The Journal of Antibiotics*, XXVIII(1):1 (1975), disclose the isolation from a fermentation broth of Streptomyces species 372A of (S)-alanyl-3-[α-(S)-chloro-3-(S)-hydroxy-2-oxo-3-azetidinyl-methyl]-(S)-alanine, which has the formula

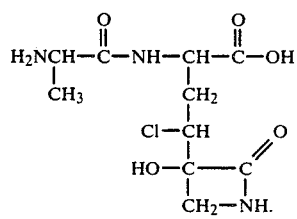

The structure of the above naturally occurring monocyclic β-lactam containing molecule is similar to the structure of the earlier discovered β-lactam containing molecules known as tabotoxins, i.e.,

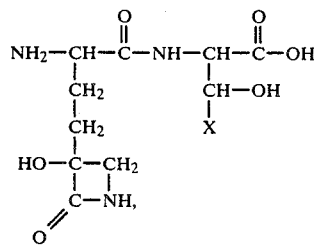

wherein X is hydrogen or methyl as reported by Stewart, *Nature*, 229:174 (1971), and Taylor et al., *Biochem. Biophys. Acta.*, 286:107 (1972).

Recently, several novel series of naturally occurring β-lactam antibiotics have been isolated. The nocardicins, nocardicin A and B, are monocyclic β-lactams having the formula

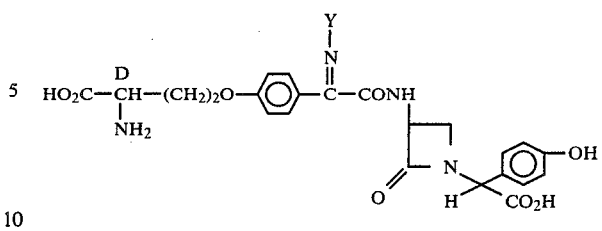

nocardicin A: Y=—syn(Z)OH
nocardicin B: Y——anti(E)OH, as reported by Hashimoto et al., *The Journal of Antibiotics*, XXIX (9):890 (1976).

Clavulanic acid, a bicyclic β-lactam antibiotic isolated from fermentation broths of Streptomyces clavuligerus, has the formula

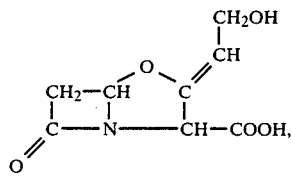

i.e., Z-(2R,5R)-3-(β-hydroxyethylidene)-7-oxo-4-oxa-1-azabicyclo[3,2,0]heptane-2-carboxylic acid, as reported by Lloyd et al., *J.C.S. Chem. Comm.*, 266 (1976).

Still another recently isolated β-lactam antibiotic is thienamycin, an antibiotic isolated from the fermentation broths of Streptomyces cattleya. As reported by Albers-Schonberg et al., *J.A.C.S.*, 100:20, 6491 (1978), thienamycin has the structure

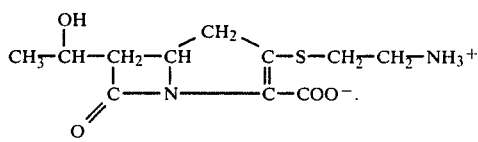

Additional fused β-lactams, olivanic acid derivatives, have recently been isolated from cultures of Streptomyces olivaceus. As disclosed by Brown et al., *J.C.S. Chem.Comm.*, these olivanic acid derivatives have the formulas

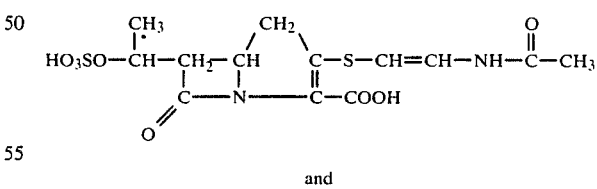

and

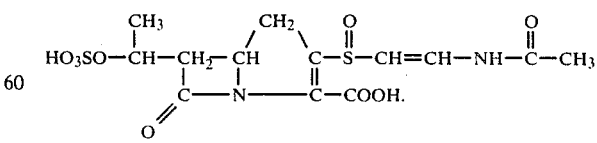

The isolation of the above antibiotics, and a discussion of their activity, is reported by Butterworth et al., *The Journal of Antibiotics*, XXXII(4):294 (1979) and by Hood et al., *The Journal of Antibiotics*, XXXII(4):295 (1979).

Another recently isolated β-lactam antibiotic is PS-5, reported by Okamura et al, *The Journal of Antibiotics*, XXXI: 480 (1978) and *The Journal of Antibiotics*, XXXII(4):262 (1979). The structure of this antibiotic, which is produced by *Streptomyces cremeus* subspecies auratilis, is reported to be

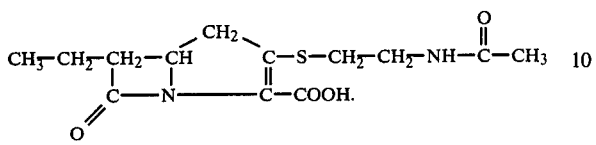

Structurally related antibiotics PS-6 and PS-7 are reported in European Patent application serial number 1,567 to have the respective structures

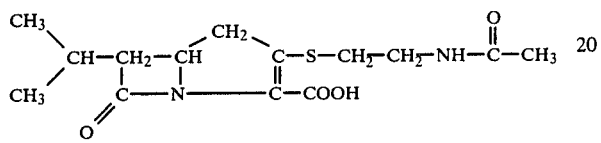

and

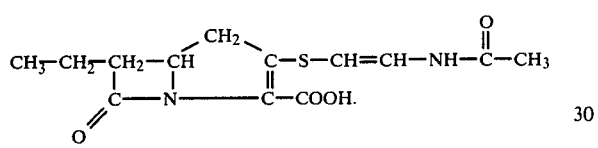

Two recently disclosed series of β-lactam antibiotics are the monocyclic β-lactams having the formulas

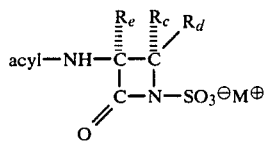

and

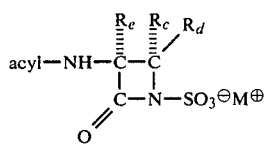

wherein $R_e$ is hydrogen or alkoxy, $R_c$ and $R_d$ are various organic substituents and $M^\oplus$ is a cation. The antibiotics having an $-SO_3^\ominus M^\oplus$ activating group are disclosed in United Kingdom patent application No. 2,071,650, published Sept. 23, 1981. The antibiotics having an $-O-SO_3^\ominus M^\oplus$ activating group are disclosed in U.S. Pat. No. 4,337,197, issued June 29, 1982.

BRIEF DESCRIPTION OF THE INVENTION

Antibacterial activity is exhibited by β-lactams having the formula

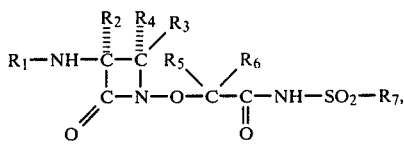

and pharmaceutically acceptable salts thereof. As used in formula I, and throughout the specification, the symbols are as defined below.

$R_1$ is acyl;

$R_2$ is hydrogen or methoxy;

$R_3$ and $R_4$ are the same or different and each is hydrogen, alkyl, alkenyl, alkynyl, cycloalkyl, phenyl, substituted phenyl or a 4,5,6 or 7-membered heterocycle (referred to hereinafter as $R_c$) or one of $R_3$ and $R_4$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$ [wherein $X_1$ is azido, amino ($-NH_2$), hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

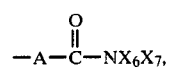

$-S-X_2$, or $-O-X_2$ (wherein A, $X_2$, $X_6$ and $X_7$ are as hereinafter defined)], $-S-X_2$ or $-O-X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

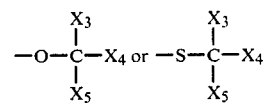

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

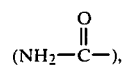

(substituted amino)carbonyl, or cyano ($-C\equiv N$)], or

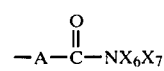

(wherein A is $-CH=CH-$, $-(CH_2)_n-$, $-CH_2-O-$, $-CH_2-NH-$, or $-CH_2-S-CH_2-$, n is 0, 1 or 2, and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ an $X_7$ when taken together with the nitrogen atom to which they are attached form a 4, 5, 6 or 7-membered heterocycle);

$R_5$ and $R_6$ are the same or different and each is hydrogen, alkyl, alkenyl, alkynyl, phenyl, substituted phenyl, cycloalkyl or $R_c$, or $R_5$ and $R_6$ together with the carbon atom to which they are attached are cycloalkyl or $R_c$, or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxy, —CH$_2$X$_1$, —S—X$_2$, —O—X$_2$, or

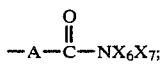

and R$_7$ is alkyl, substituted alkyl, phenyl or substituted phenyl.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino (—NH$_2$), halogen, hydroxy, carboxy, cyano, alkoxycarbonyl, aminocarbonyl, alkanoyloxy, alkoxy, phenyloxy, (substituted phenyl)oxy, R$_c$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino(—NH$_2$), halogen, hydroxyl, trifluoromethyl, alkyl (of 1 to 4 carbon atoms), alkoxy (of 1 to 4 carbon atoms), carbamyl, or carboxyl groups.

The expression "a 4,5,6 or 7-membered heterocycle" (referred to as "R$_c$") refers to substituted and unsubstituted, aromatic and non-aromatic groups containing one or more nitrogen, oxygen or sulfur atoms. Exemplary substituents are oxo(=O), halogen, hydroxy, nitro, amino, cyano, trifluoromethyl, alkyl of 1 to 4 carbons, alkoxy of 1 to 4 carbons, alkylsulfonyl, phenyl, substituted phenyl, and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substitutd phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-furanyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NY$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy, or amino (—NH$_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

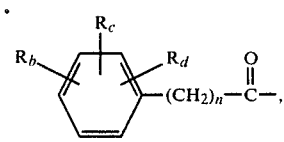

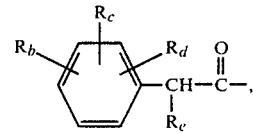

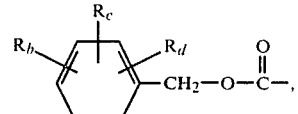

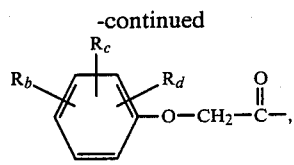

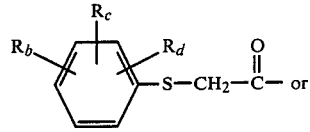 or

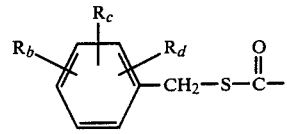

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

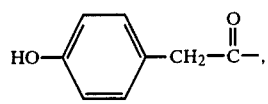

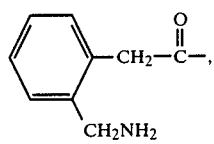

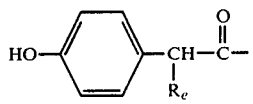

($R_e$ is preferably a carboxyl salt or sulfo salt) and

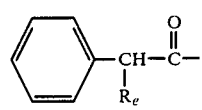

($R_e$ is preferably a carboxyl salt or sulfo salt).

(c) Heteroaromatic groups having the formula

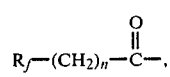

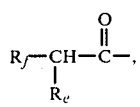

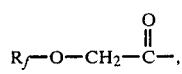

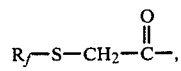

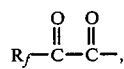

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or $$HOOC-\underset{\underset{NH_2}{|}}{CH}-CH_2-O-\overset{\overset{O}{\|}}{C}-NH-.$$

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

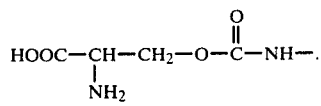

wherein $R_g$ is an aromatic group (including carbocyclic aromatics such as those of the formula

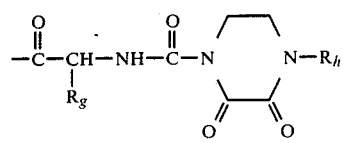

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e.,

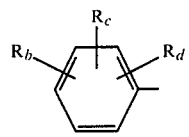

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

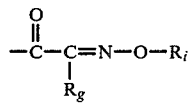

wherein $R_g$ is as defined above and $R_i$ is hydrogen, alkyl, cycloalkyl, alkylaminocarbonyl, arylaminocarbonyl (i.e.,

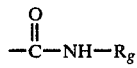

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

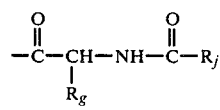

wherein $R_g$ is as defined above and $R_j$ is

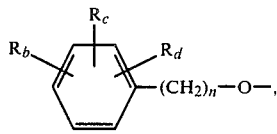

amino, alkylamino, (cyanoalkyl)amino, amido, alkylamido, (cyanoalkyl)amido,

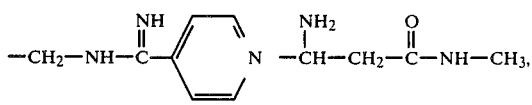

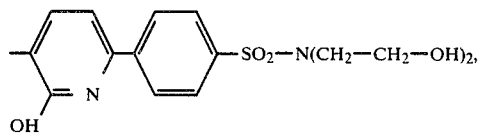

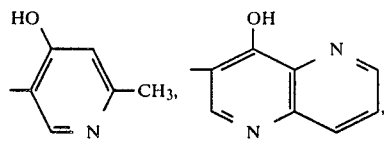

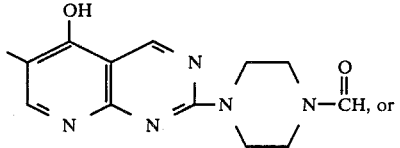

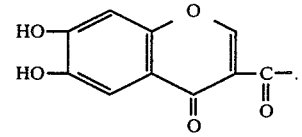

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

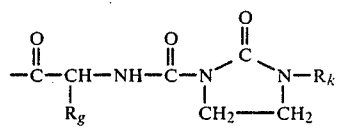

wherein $R_g$ is as defined above and $R_k$ is hydrogen, alkylsulfonyl, arylmethyleneamino (i.e., $-N=CH-R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases water of hydration may be formed. This invention contemplates stoichiometric hydrates as well as compounds containing variable amounts of water that may be produced by processes such as lyophilization.

β-Lactams having an $$-\text{O}-\underset{\text{R}_5}{\overset{\text{R}_6}{\text{C}-\text{C}}}-\text{NH}-\text{SO}_2-\text{R}_7$$
$$\underset{\text{O}}{\|}$$

substituent in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

Also included within the scope of this invention are racemic mixtures which contain the above-described β-lactams.

DETAILED DESCRIPTION OF THE INVENTION

β-Lactams having an $$-\text{O}-\underset{\text{R}_5}{\overset{\text{R}_6}{\text{C}-\text{C}}}-\text{NH}-\text{SO}_2-\text{R}_7$$
$$\underset{\text{O}}{\|}$$

substituent in the 1-position of the β-lactam nucleus and an acylamino substituent in the 3-position of the β-lactam nucleus have activity against a range of gram-negative and gram-positive organisms.

The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The β-lactams of this invention can be prepared from an amino acid having the formula $$\text{NH}_2-\text{CH}-\overset{\text{OH}\quad\text{R}_4}{\underset{\underset{\text{O}}{\overset{\|}{\text{C}}-\text{OH}}}{\text{C}-\text{R}_3}}$$
II The amino group is first protected with a classical protecting group (e.g., t-butoxycarbonyl, benzyloxycarbonyl, o-nitrophenylsulfenyl, etc.), yielding a compound having the formula $$\text{A}_1-\text{NH}-\text{CH}-\overset{\text{OH}\quad\text{R}_4}{\underset{\underset{\text{O}}{\overset{\|}{\text{C}}-\text{OH}}}{\text{C}-\text{R}_3}}$$
III In formula III, and throughout the specification, the symbol "A$_1$" refers to a nitrogen protecting group.

The carboxyl group of a protected amino acid of formula III is then reacted with an amine salt having the formula $$\text{Y}-\text{O}-\text{NH}_3^{\oplus}\text{Cl}^{\ominus}.$$
IV In formula IV, and throughout the specification, the symbol "Y" refers to benzyl, pivaloyl, —CH$_2$CH(NHA$_2$)CO$_2$alkyl (A$_2$ is an amino protecting group), t-butyl, p-nitrobenzyl, benzhydryl, 2-cyanoethyl, 2-trimethylsilylethyl, trichloroethyl, p-anisyl, inter alia. The reaction proceeds in the presence of a coupling agent such as 1-ethyl-3-(3-dimethylaminopropyl)carbodiimide or dicyclohexylcarbodiimide, and yields a compound having the formula $$\text{A}_1-\text{NH}-\text{CH}-\overset{\text{OH}\quad\text{R}_4}{\underset{\underset{\text{O}}{\overset{\|}{\text{C}}-\text{NH}-\text{O}-\text{Y}.}}{\text{C}-\text{R}_3}}$$
V The hydroxyl group of a compound of formula V is converted to a leaving group, using, for example, a classical reagent such as methanesulfonyl chloride (methanesulfonyl is referred to hereinafter as "Ms").

The fully protected compound having the formula $$\text{A}_1-\text{NH}-\text{CH}-\overset{\text{OMs}\quad\text{R}_4}{\underset{\underset{\text{O}}{\overset{\|}{\text{C}}-\text{NH}-\text{O}-\text{Y}}}{\text{C}-\text{R}_3}}$$
VI is cyclized by treatment with base, e.g., potassium carbonate. The reaction is preferably carried out in an organic solvent such as acetone, under reflux conditions, and yields a compound having the formula $$\text{A}_1-\text{NH}-\text{CH}-\overset{\text{R}_4}{\underset{\underset{\text{O}}{\overset{\|}{\text{C}}-\!\!-\text{N}-\text{O}-\text{Y}.}}{\text{C}-\text{R}_3}}$$
VII Alternatively, cyclization of a compound of formula V can be accomplished without first converting the hydroxyl group to a leaving group. Treatment of a compound of formula V with triphenylphosphine and diethylazodicarboxylate or carbon tetrachloride, yields a compound of formula VII.

Both of the methods disclosed above for ring closure of a compound of formula V result in the inversion of the stereochemistry of the R$_3$ and R$_4$ substituents.

Selective reduction of a compound of formula VII (using catalytic hydrogenation if Y is benzyl or by treatment with a base such as sodium sulfide or sodium hydroxide if Y is pivaloyl, or with DBU if Y is —CH$_2$CH(NHA$_2$)CO$_2$alkyl) yields the corresponding compound having the formula

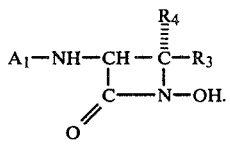
VIII

Compounds of formula VIII are described in copending U.S. patent application Ser. No. 404,945, filed Aug. 4, 1982 and some are also described in *J.A.C.S.*, 102:7026 (1980).

Alkylation of a hydroxamic acid of formula VIII with an activated and protected (if needed) form of a compound having the formula

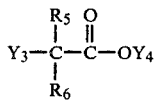
IX can be accomplished by first generating the anion of the hydroxamic acid with a suitable base, and then reacting the resulting compound with an activated form of an acetic acid derivative of formula IX. In formula IX, and throughout the specification, Y$_3$ is a suitable leaving group, such as a halogen atom (preferably bromine or chlorine), a mesylate or triflate group, or any of the other leaving groups well known in the art, and Y$_4$ is a carboxylic acid protecting group that can be selectively removed in the presence of A$_1$. The above alkylation procedure has been described as a two step sequence, but both steps can be performed simultaneously. The resulting product has the formula

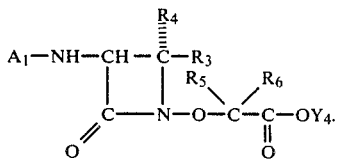
X

Removal of the Y$_4$ protecting group from a compound of formula X, followed by treatment with a sulfonyl isocyanate having the formula

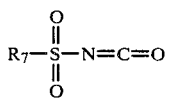
XI in the presence of an organic base, e.g., triethylamine, yields the corresponding compound having the formula

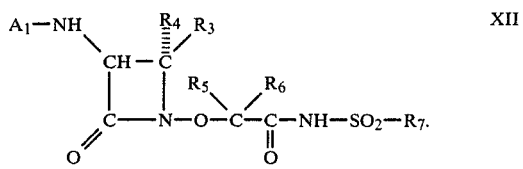
XII

Deprotection of the 3-amino substituent of a compound of formula XII can be accomplished using art-recognized techniques. If, for example, the protecting group is t-butoxycarbonyl, trifluoroacetic acid can be used to deprotect the amino group. If the protecting group is benzyloxycarbonyl, catalytic (e.g., palladium on charcoal) hydrogenation can be used. If the protecting group is o-nitrophenylsulfenyl, p-toluenesulfonic acid can be used in combination with p-thiocresol. The deprotected compound has the formula

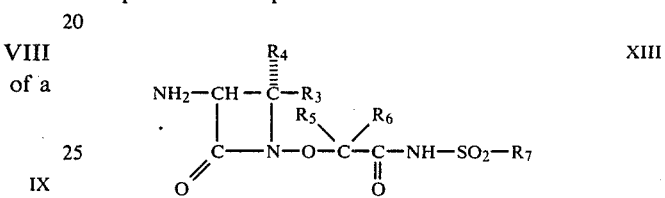
XIII and is a key intermediate for preparing the compounds of this invention. The compounds of formula XIII form an integral part of this invention.

Well known acylation techniques can be used to convert a compound of formula XIII to the corresponding compound having the formula

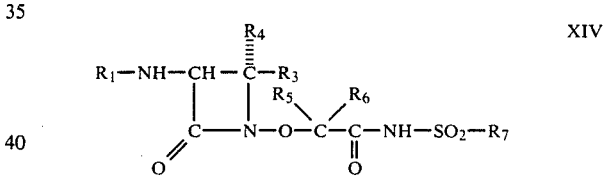
XIV

Exemplary techniques include reaction with a carboxylic acid (R$_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group (R$_1$) contains reactive functionality (such as amino or carboxy groups) it may be necessary to first protect these functional groups, then carry out the acylation reaction, and finally deprotect the resulting product.

The products of formula I wherein R$_2$ is methoxy can be prepared from the corresponding compound of formula VII. Halogenating (preferably chlorinating) the amide nitrogen of a compound of formula VII yields a compound having the formula

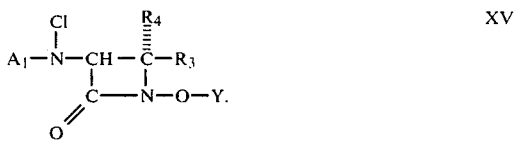
XV

Reagents and procedures of N-chlorinating amides are known in the art. Exemplary reagents are tert.-butyl hypochlorite, sodium hypochlorite, and chlorine. The reaction can be run in an organic solvent (e.g., a lower alkanoyl such as methanol) or in a two phase solvent system (e.g., water/methylene chloride) in the presence of a base such as sodium borate decahydrate. The reaction is preferably run at a reduced temperature.

Reaction of a compound of formula XV with a methoxylating agent, e.g., an alkali metal methoxide, yields a compound (in combination with its enantiomer if $R_3$ and $R_4$ are the same or if XV is a racemic mixture) having the formula

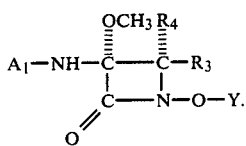  XVI

The reaction can be run in an organic solvent, e.g., a polar organic solvent such as tetrahydrofuran, at a reduced temperature.

Alternatively, a compound of formula VII can be converted to a compound of formula XVI using a single step procedure. The methoxylating agent can first be mixed with a compound of formula VII and the N-chlorinating reagent then added to the reaction mixture.

Conversion of a compound of formula XVI to the desired products of formula I can be accomplished using the procedures described above for the conversion of an intermediate of formula VII to a product of this invention.

The following examples are specific embodiments of this invention.

EXAMPLE 1

[3S-[3α(Z),4β]]-2-Amino-α-(methoxyimino)-N-[4-methyl-1-[2-[(methylsulfonyl)amino]-2-oxoethoxy]-2-oxo-3-azetidinyl]-4-thiazoleacetamide, potassium salt (A)

(3S-trans)-3-[[(1,1-Dimethylethoxy)carbonyl]amino]-4-methyl-1-[[(phenylmethoxy)carbonyl]methoxy]-2-acetidinone 3-[[(1,1-Dimethylethoxy)carbonyl]amino]-4-methyl-1-(phenylmethoxy)-2-azetidinone (6.25 g, 20.4 mmol) was dissolved in 100 ml of ethanol and 10% palladium on charcoal (4.0 g) was added under argon. Hydrogenolysis (1 atmosphere, 20° C.) was completed in 1.5 hours. The reaction mixture was filtered and the volatiles were removed. The residue was dissolved in dimethylformamide (80 ml), and benzyl bromoacetate (5.46 g) was added, followed by anhydrous potassium carbonate (8.00 g). After 2 hours at 20° C., the reaction mixture was poured into ice-cold dilute hydrochloric acid and extracted four times with ethyl acetate. The combined organic layers were washed twice with water and dried with sodium sulfate. The volatiles were removed and the residue was subjected to column chromatography (Mallinckrodt CC-7 silica, eluting with 35% ethyl acetate/hexane) yielding 8.01 g of the title compound.

(B)

(3S-trans)-3-[[(1,1-Dimethylethoxy)carbonyl]amino]-1-[2-[(methylsulfonyl)amino]-2-oxoethoxy]-4-methyl-2-azetidinone, potassium salt (3S-trans)-3-[[(1,1-Dimethylethoxy)carbonyl]amino]-4-methyl-1-[[(phenylmethoxy)carbonyl]methoxy]-2-azetidinone (0.73 g, 2.0 mmol) was dissolved in 12 ml of absolute ethanol and 0.36 g of 10% palladium on charcoal was added under argon. Hydrogenolysis (1 atmosphere, 20° C.) was completed in 30 minutes. The reaction mixture was filtered and the volatiles were removed to yield 0.55 g of crude (3S-trans)-3-[[(1,1-dimethylethoxy)carbonyl]amino]-4-methyl-1-(carboxymethoxy)-2-azetidinone.

The free acid (0.55 g, ~2.0 mmole) was dissolved in acetonitrile (10 ml) and 0.3 ml (2.1 mmol) of triethylamine was added. Upon cooling to 0° C., methanesulfonyl isocyanate (170 μl, 2.0 mmol) was added, and the reaction mixture was allowed to warm to room temperature. After 4 hours, the volatiles were removed, and the residue was dissolved in aqueous potassium bicarbonate. The bicarbonate solution was subjected to Dowex ($K^+$ form) chromatography (eluting with water) followed by chromatography on HP-20 (eluting with water and 5% acetone-water) yielding 499 mg of the title compound.

(C)

[3S-[3α(Z),4β]]-2-Amino-α-(methoxyimino)-N-[4-methyl-1-[2-[(methylsulfonyl)amino]-2-oxoethoxy]-2-oxo-3-azetidinyl]-4-thiazoleactamide, potassium salt Diisopropylethylamine (0.073 ml, 0.42 mmol) was added to 76 mg (0.38 mmol) of (Z)-2-amino-α-(methoxyimino)-4-thiazoleacetic acid in 1.0 ml of dimethylformamide at 23° C. The mixture was cooled to −20° C., diphenyl chlorophosphate (0.078 ml, 0.38 mmol) was added, and the resulting mixture was stirred for 30 minutes to yield (Z)-2-amino-α-(methoxyimino)acetic acid, diphenyl phosphate ester.

(3S-trans)-3-[[(1,1-Dimethylethoxy)carbonyl]amino]-1-[2-[(methylsulfonyl)amino]-2-oxoethoxy]-4-methyl-2-azetidinone, potassium salt (117 mg., 0.30 mmol) was suspended in 0.15 ml of anisole and cooled to 0° C. Trifluoroacetic acid (1.5 ml) was added, and the resulting mixture was stirred at 0° C. for 30 minutes. The volatiles were evaporated, and the residue was triturated with petroleum ether and anhydrous ether. After evacuation for 15 minutes, the residue was cooled to 0° C. and dissolved in 1.0 ml of water. The pH was adjusted to ~7 with solid potassium bicarbonate. (Z)-2-Amino-α-(methoxyimino)-4-thiazoleacetic acid, diphenyl phosphate ester was added, the pH was readjusted to pH ~7, and the reaction was stirred at 5° C. overnight.

The volatiles were removed under vacuum. The residue was purified by column chromatography (eluting with water) on Dowex 50X-200 resin ($K^+$ form) followed by chromatography on HP-20 (eluting with water) to give 67 mg of the title compound, melting point 165°–175° C., dec.

What is claimed is:

1. A β-lactam having the formula

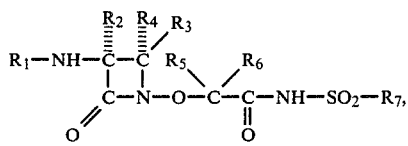

or a pharmaceutically acceptable basic salt thereof, wherein $R_1$ is an acyl group derived from a carboxylic acid;
$R_2$ is hydrogen or methoxy;
$R_3$ and $R_4$ are the same or different and each is hydrogen, alkyl, alkenyl, alkynyl, cycloalkyl, phenyl, substituted phenyl or a 4,5,6 or 7-membered heterocycle or one of $R_3$ and $R_4$ is hydrogen and the other is azido, halomethyl, dihalomethyl, trihalomethyl, alkoxycarbonyl, alkenyl, alkynyl, 2-phenylethenyl, 2-phenylethynyl, carboxyl, —CH$_2$X$_1$, —S—X$_2$, —O—X$_2$,

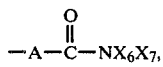

wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

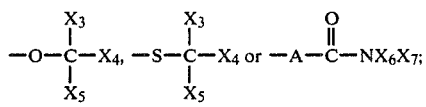

—S—X$_2$ or —O—X$_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —(CH$_2$)$_n$—, —CH$_2$—O—, —CH$_2$—NH— or —CH$_2$—S—CH$_2$—; n is 0, 1 or 2; and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle; and $R_5$ and $R_6$ are the same or different and each is hydrogen, alkyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxyl, —CH$_2$X$_1$, —S—X$_2$, —O—X$_2$, or

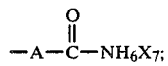

and $R_7$ is alkyl, substituted alkyl, phenyl or substituted phenyl;

wherein the terms "alkyl" and "alkoxy" refer to grounds having 1 to 10 carbon atoms;

the term "cycloalkyl" refers to groups having 3, 4, 5, 6 or 7 carbon atoms;

the terms "alkanoyl", "alkenyl", and "alkynyl", refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, carbamyl, or carboxyl groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (heteroaryl)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;

the term "substituted amino" refers to a group having the formula —NY$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy or amino.

2. A compound in accordance with claim 1 wherein $R_2$ is hydrogen.

3. A compound in accordance with claim 1 wherein $R_3$ and $R_4$ are the same or different and each is hydrogen, methyl, ethyl, carbamyl, methoxymethyl, fluoromethyl, methoxycarbonyl, or acetyloxymethyl.

4. A compound in accordance with claim 1 wherein $R_3$ and $R_4$ are the same or different and each is hydrogen or methyl.

5. A compound in accordance with claim 1 wherein $R_3$ and $R_4$ are each hydrogen.

6. A compound in accordance with claim 1 wherein $R_5$ and $R_6$ are the same or different and each is hydrogen, methyl, ethyl, or methoxy.

7. A compound in accordance with claim 1 wherein each of $R_2$, $R_3$, $R_4$, $R_5$ and $R_6$ is hydrogen.

8. A compound in accordance with claim 1 wherein $R_1$ is

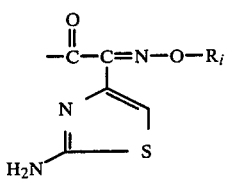

and $R_i$ is methyl, ethyl, carboxymethyl, 1-carboxy-1-methylethyl or 2,2,2-trifluoroethyl.

9. A compound in accordance with claim 1 wherein $R_1$ is

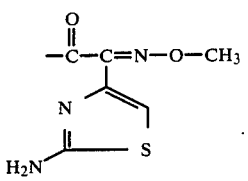

10. A compound in accordance with claim 1 wherein $R_1$ is

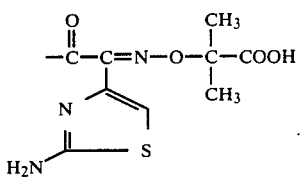

11. The compound in accordance with claim 1, [3S-[3α(Z),4β]]-2-Amino-α-(methoxyimino)-N-[4-methyl-1-[2-[(methylsulfonyl)amino]-2-oxoethoxy]-2-oxo-3-azetidinyl]-4-thiazoleactamide, potassium salt.

12. A β-lactam having the formula

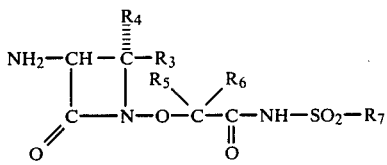

wherein $R_3$ and $R_4$ are the same or different and each is hydrogen, alkyl, alkenyl, alkynyl, cycloalkyl, phenyl, substituted phenyl or a 4,5,6 or 7-membered heterocycle or one of $R_3$ and $R_4$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$, $-S-X_2$, $-O-X_2$,

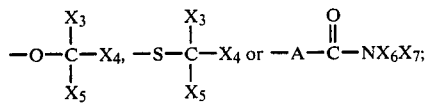

wherein $X_1$ is azido, amino, hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

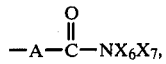

$-S-X_2$ or $-O-X_2$; $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of $X_3$ and $X_4$ is hydrogen and the other is hydrogen or alkyl, or $X_3$ and $X_4$ when taken together with the carbon atom to which they are attached form a cycloalkyl group; $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is $-CH=CH-$, $-(CH_2)_n-$, $-CH_2-O-$, $-CH_2-NH-$ or $-CH_2-S-CH_2-$; n is 0, 1 or 2; and $X_6$ and $X_7$ are the same or different and each is hydrogen, alkyl, phenyl or substituted phenyl, or $X_6$ is hydrogen and $X_7$ is amino, substituted amino, acylamino or alkoxy, or $X_6$ and $X_7$ when taken together with the nitrogen atom to which they are attached form a 4, 5, 6 or 7-membered heterocycle; and $R_5$ and $R_6$ are the same or different and each is hydrogen, alkyl, alkenyl, alkynyl, phenyl, substituted phenyl, cycloalkyl or a 4, 5, 6 or 7-membered heterocycle, or $R_5$ and $R_6$ together with the carbon atom to which they are attached are cycloalkyl or a 4, 5, 6 or 7-membered heterocycle or one of $R_5$ and $R_6$ is hydrogen and the other is azido, halomethyl, dihalomethyl, trihalomethyl, alkoxycarbonyl, alkenyl, alkynyl, 2-phenylethenyl, 2-phenylethynyl, carboxyl, $-CH_2X_1$, $-S-X_2$, $-O-X_2$, or

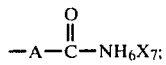

and $R_7$ is alkyl, substituted alkyl, phenyl or substituted phenyl;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", and "alkynyl", refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, carbamyl, or carboxyl groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substitued phenyl)oxy, (heteroaryl)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolylidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;

the term "substituted amino" refers to a group having the formula $-NY_1Y_2$ wherein $Y_1$ is hydrogen, alkyl, phenyl, substituted phenyl, phenylalkyl or (substituted phenyl)alkyl, and $Y_2$ is alkyl, phenyl, substituted phenyl, phenylalkyl, (substituted phenyl)alkyl, hydroxy, cyano, alkoxy, phenylalkoxy or amino.

* * * * *